(12) United States Patent
Thieme et al.

(10) Patent No.: US 9,989,946 B2
(45) Date of Patent: Jun. 5, 2018

(54) LABORATORY MACHINE AND METHOD FOR THE AUTOMATIC TREATMENT OF LABORATORY SAMPLES

(71) Applicant: Eppendorf AG, Hamburg (DE)

(72) Inventors: Andreas Thieme, Hamburg (DE); Claas Huesmann, Bremen (DE); Stefan Roth, Hambrug (DE); Judith Lucke, Hamburg (DE); Harald Pohl, Hamburg (DE)

( * ) Notice: Subject to any disclaimer, the term of this patent is extended or adjusted under 35 U.S.C. 154(b) by 827 days.

(21) Appl. No.: 14/043,737

(22) Filed: Oct. 1, 2013

(65) Prior Publication Data

US 2014/0094971 A1    Apr. 3, 2014

Related U.S. Application Data

(60) Provisional application No. 61/708,064, filed on Oct. 1, 2012.

(30) Foreign Application Priority Data

Oct. 1, 2012   (EP) .................................... 12006836

(51) Int. Cl.
*G05B 19/02* (2006.01)
*G01N 35/00* (2006.01)

(52) U.S. Cl.
CPC ....... *G05B 19/02* (2013.01); *G01N 35/00722* (2013.01); *G01N 2035/0091* (2013.01)

(58) Field of Classification Search
None
See application file for complete search history.

(56) References Cited

U.S. PATENT DOCUMENTS

| | | | | |
|---|---|---|---|---|
| 6,159,693 A | * | 12/2000 | Shultz ................... | C12Q 1/04 435/17 |
| 6,326,147 B1 | * | 12/2001 | Oldham ............. | G01N 35/0092 422/50 |
| 6,442,440 B1 | * | 8/2002 | Miller ................... | G06F 3/0482 700/83 |
| 2004/0117124 A1 | * | 6/2004 | Kiros ................. | G01N 15/1475 702/19 |
| 2004/0158433 A1 | | 8/2004 | Wimschneider et al. | |
| 2006/0048846 A1 | * | 3/2006 | Roenneburg ........... | G01N 30/88 141/130 |
| 2006/0178776 A1 | * | 8/2006 | Feingold ............ | G01N 35/0092 700/245 |
| 2007/0184546 A1 | | 8/2007 | Farrelly et al. | |

(Continued)

FOREIGN PATENT DOCUMENTS

| | | |
|---|---|---|
| JP | 2008-35841 A | 2/2008 |
| WO | WO 2009/130318 A2 | 10/2009 |

*Primary Examiner* — Mohammad Ali
*Assistant Examiner* — Bernard G Lindsay
(74) *Attorney, Agent, or Firm* — Todd A. Lorenz (57) ABSTRACT

The invention relates to a program-controlled laboratory machine and to a method for the automatic program-controlled treatment of laboratory samples. The laboratory machine has a display having a first display area, via which program parameters that are required by the user are input, and has a second display area in which these input program parameters are shown. The performance of the treatment is effected automatically using the program parameters that are required by the user.

17 Claims, 3 Drawing Sheets

(56) References Cited

U.S. PATENT DOCUMENTS

| | | | |
|---|---|---|---|
| 2010/0105074 A1 | 4/2010 | Covey et al. | |
| 2011/0046910 A1* | 2/2011 | Haas | G01N 35/00871 |
| | | | 702/108 |
| 2011/0104679 A1* | 5/2011 | DeAngelis | C12Q 1/6883 |
| | | | 435/6.16 |
| 2011/0160909 A1* | 6/2011 | Glauser | G01N 35/00722 |
| | | | 700/264 |
| 2012/0004742 A1 | 1/2012 | Wakamiya et al. | |
| 2012/0109529 A1* | 5/2012 | Ariyoshi | G01N 1/312 |
| | | | 702/19 |
| 2012/0304096 A1* | 11/2012 | Shikhman | G06Q 10/06 |
| | | | 715/771 |
| 2013/0316336 A1 | 11/2013 | Matsui et al. | |
| 2014/0046484 A1 | 2/2014 | Glauser et al. | |

\* cited by examiner

Fig. 2

LABORATORY MACHINE AND METHOD FOR THE AUTOMATIC TREATMENT OF LABORATORY SAMPLES

The invention relates to a laboratory machine and to a method for the automatic treatment of laboratory samples.

Such laboratory machines are used in order to handle samples, in particular liquid samples, with a high level of efficiency in chemical, biological, biochemical, medical or forensic laboratories. Laboratory machines automate treatment steps that would otherwise have to be performed manually, and in this way increase the speed, precision and reliability of these treatment operations.

Treatment of a liquid laboratory sample can be directed at changing a composition of this sample physically, chemically, biochemically or in another way. Treatment of the sample allows a sample to be divided or diluted, for example. The contents of a sample can be analysed or new contents can be produced, for example by a chemical reaction, particularly by using the sample. Particularly in connection with the handling and analysis of DNA or RNA or the constituents thereof, laboratory machines are useful in order to obtain a wealth of information within a suitable period of time or to analyse a large number of such samples.

Laboratory machines usually have a work surface with workstations on which samples can be handled or stored in different ways. For the transport of liquid samples between different positions, particularly sample containers, for example, a program-controlled movement apparatus is usually used in conjunction with a fluid transfer device, which may have a pipetting system, for example. Both the transport of the samples and the treatment thereof on the different stations can be automated under program control.

The programming of known laboratory machines has often been described as incommodious and not very user friendly. Occasionally, the user has had to acquire programming knowledge himself in order to be able to perform the device-specific programming. In this case, known laboratory machines have the problem that a control program is usually input in unstructured fashion by virtue of the program as a whole being written in an editor. The programmer not only needs to concern himself with the correct choice of program parameters and conversion formulae but also, at the same time, needs to concern himself with error-free program logic and correct syntax for the programming language. Some laboratory machines on the market now afford input systems in which a stipulated number of program parameters are captured in a dedicated manner by means of displays and input options on a laboratory machine. Often, these input programs are limited to being used with manufacturer-specific accessory kits and are therefore complicated and inflexible for performing the large number of applications that the user desires.

US 2011/0160909 A1 describes a motorized pipetting workstation, wherein the positioning and the action of the pipette tool is computer controlled and remote controlled. For this purpose, the workstation displays a visualization of the pipette and the pipette positions by means of a user interface having a display, in particular a touch screen. US 2007/0184546 A1 describes an automated pipetting apparatus, which uses a display for visualizing the working steps of a running automatic treatment of samples, wherein the display has more than one display area. US 2010/0105074 A1 describes a high throughput process and system for analyzing cells using a flow cytometer. The system has a automated liquid handling unit for the transfer, mixing, centrifuging of liquid samples contained in well plates. US 2004/0158433 A1 describes an apparatus for the automated analysis of liquid samples, wherein the results of the sample analysis are transferred to a control device for the purpose of adapting a subsequent process. US 2012/0004742 A1 describes an apparatus for the analysis of samples, which comprises a data memory device, a display and a control device, which is used to display a visualization of the maintenance status of the apparatus using a calendar form. The documents, respectively, are not related to improving the visualization structure of a user interface and do not describe the implementation of a user interface including a particular structure having a display area for data input and a further display area for data output according to the present invention.

It is an object of the present invention to provide a laboratory machine and a method for the automatic treatment of laboratory samples that are simple and flexible to use.

The invention achieves this object particularly by means of the laboratory machine according to Claim 1 and the method according to Claim 14. Preferred embodiments are particularly subjects of the subclaims.

The inventive laboratory machine for the program-controlled treatment of at least one laboratory sample has:
a treatment device for the automatic, program-controlled treatment of the at least one laboratory sample, wherein the treatment is controlled by using a plurality of program parameters that are chosen at least in part by the user,
an electronic control device having
at least one processor device for data processing, particularly for executing a control program for controlling the laboratory machine,
having at least one memory device for storing data, particularly the control program and the program parameters,
a user interface device for the manual input of data by a user, and for the display of information, particularly of information that these data contain, wherein the user interface device has a display, particularly a touch-screen display,
and this at least one control program for controlling the laboratory machine, wherein the at least one control program contains instructions in order to perform the following steps:
(a) display of at least one query area in a first display area of the display, wherein a query area has at least one information area and at least one input area associated with this at least one information area,
(b) progressive querying of program parameters that are required for the program-controlled execution of the treatment by virtue of a piece of information for the at least one program parameter being displayed in the at least one information area and an input from the user, particularly a touch on the at least one input area, being captured in the at least one input area,
(c) in each case following input of at least one program parameter by the user, either immediately following input by the user or after the user has made several inputs, particularly after he has made all inputs that are required by the user: display of the at least one value that is input by the user for the at least one program parameter in an information area of the second display area of the display,
wherein preferably, following the querying of these required program parameters, one, a plurality of or all value(s) input by the user for these program parameters is/are displayed in this second display area, (d) performance of the treatment by using the queried program parameters.

The inventive laboratory machine affords the advantage that the program parameters are input in a structured manner by virtue of the input being made in a first display area by means of one or more query areas, the result of this input, including the description of the associated program parameters, always being displayed to the user in a second display area. As a result, the user is provided with an overview of the already input data at any time in the stipulation of the program parameters.

If the display is a touchscreen display, the laboratory machine can be operated in particularly intuitive and convenient fashion. In addition, a touchscreen display is low maintenance, in particular easier to clean, to decontaminate or sterilize than conventional operator control elements, particularly those that have mechanically movable parts. A touchscreen display may be of a design that is resistant to chemicals, which is very advantageous in particular laboratory environments. Alternatively, the display may not be provided for input and may be limited to the display function. In that case, input is made using a pointing device, e.g. an operator control element of the user interface device, that moves a pointing object on the display, in the manner of a mouse pointer, which can be used to make an input or selection. The user interface device may also have a keypad.

The display is preferably able to display a substantially rectangular display area, as is customary with such displays. Preferably, the first display area is substantially rectangular. Preferably, the second display area is substantially rectangular. Further display areas may be provided, e.g. a title bar and/or a base bar, and/or a border bar and/or a navigation bar. Preferably, the first and second display areas are presented horizontally next to one another. This is particularly advantageous in case of a screen ratio in which the horizontal length of the display size ("display width B") is greater than the vertical length of the display size ("display height H"). In this way, the first display area can be used to present the query areas having information and input panels and the second display area can be used to present the information particularly clearly below one another, which is preferred. The laboratory machine can thus be controlled even more intuitively and conveniently. It is also possible and preferred for the first and second display areas to be presented vertically below one another. This can apply particularly when H>B. The scrolling of a list presented in the first display area can, particularly if H>B, also take place in a horizontal direction.

Preferably, the height H1 of the first display area is substantially the same as the height H2 of the second display area. This allows optimum use of the available display height H, in particular. The laboratory machine can thus be controlled even more intuitively and conveniently. It is also possible for H1 to be not equal to H2.

Preferably, the width B1 of the first display area is substantially greater than the width B2 of the second display area, particularly when the first and second display areas are displayed horizontally next to one another. This allows the program parameters in the first display area to be queried conveniently, while the presentation in the second display area can be kept compact and clear, which is consistent with the aim of presenting the already input parameters in the second display area. The laboratory machine can thus be controlled even more intuitively and conveniently.

An information area and/or the query area may each preferably be substantially rectangular, or circular, or of a different shape, in particular may be an elemental detail from the first or second display area. An information area is used to display a piece of information to the user, e.g. the description of a program parameter to be queried. An input area is used for the user to make an input, particularly by selecting the input area and/or input in this input area, which input is then processed by the laboratory machine, particularly to derive a program parameter therefrom or to use the input directly as a program parameter, and which input is stored, in particular. The input area can provide the selection from a collection of values and/or details, particularly as a list, in particular from a "pop-up" list, and/or the input of a text, particularly a value.

The first and second display areas are displayed particularly when at least one, a plurality of or all parameter(s) required by the user is/are queried. This display therefore takes place at least intermittently during the operation of the laboratory machine. It is also possible for at least one parameter required by the user to be queried when the display does not display the first and/or the second display area. The first and second display areas can each also be used for a purpose other than the steps described in steps a) and b).

Furthermore, the laboratory machine is preferably designed such that the treatment of the at least one laboratory sample can be controlled automatically by using the captured program parameters. The laboratory machine, particularly the control program thereof, is preferably designed such that the inputs made by the user, particularly the at least one value of at least one program parameter, are used to automatically ascertain any further required program parameters, particularly by means of calculation or by means of comparison with data in a database of the laboratory machine. In particular, the control parameters that are specifically preferably intended to be used for performing the treatment are preferably determined automatically. These measures make the operation of the laboratory machine convenient, and the user is spared particularly the design of a program code, since these steps are performed, in particular automatically, by the laboratory machine. In one preferred refinement of the invention, the user requests only the inputs that are directly involved with the treatment to be performed on the samples. These are frequently the same details that would also be necessary for manual performance of the treatment and with which the user is familiar. By contrast, such parameters as relate to the control of the laboratory machine, particular the control parameters, do not need to be stipulated specifically, since they are preferably stipulated automatically. Control parameters are the parameters that are specifically required for controlling the technical parts of the treatment device. Control parameters may be program parameters or may be parameters derived therefrom for the technical implementation, in particular may be automatically determined parameters.

Program controlled treatment of a sample is intended to be understood to mean that the procedure of the treatment is controlled substantially automatically, specifically in line with the provisions of a computer program. In particular, essentially no user activity is required in the case of program-controlled treatment, at least following capture of the program parameters that are required by the user.

A program parameter is understood to mean a variable that can be used to "set" a computer program or subroutine, valid for a call, to particular values. These settings are taken into account during the processing and thus usually also influence the results of the program. A program parameter may be a program parameter that is required by the user, that is to say an influential factor that is set externally to the program. A program parameter that is required by the user is distinguished in that it is required for executing a treatment, particularly for executing a method program. Other program parameters that are not required by the user can be derived from the program parameters that are required by the user or can be made available in another way.

An instruction usually denotes a central element of a programming language. The programs in such languages are made up primarily of one or more instructions. An instruction is a single rule that is formulated in the syntax of a programming language and that needs to be executed during the execution of the program. The syntactic appearance that an instruction needs to have is stipulated by the respective programming language or the specification thereof. In machine-level programming, instructions are frequently also called commands.

Instructions are usually assignments, control assignments (such as jumps, loops and conditional instructions) and procedure calls. Depending on the programming language, assertions, declarations, class and function definitions are sometimes also instructions. The instructions in the control program may thus be in customary form.

A program module is usually understood to mean a self-contained functional unit of a piece of software, comprising a series of processing steps and data structures. In this case, the following definitions may apply, in particular: the content of a module is frequently a recurring calculation up or handling of data that needs to be carried out repeatedly. Modules afford encapsulation through the division of interface and implementation: the interface of a module defines the data elements that are required as an input and a result of the processing by the module. The implementation contains the actual program code. A module is called as a function or subroutine, for example, performs a series of processing steps and returns data to the calling program as the result. A module can itself call further modules—thus, a hierarchy of program calls is possible. The data structures and methods stipulated in modules can possible be handed down, and inherited from other modules. Modules are therefore an essential element in the structured and object-oriented programming.

A control program is understood to mean an executable computer program that brings about the desired automatic treatment of at least one sample on the basis of the program parameters, particularly the program parameters that are required by the user and the further program parameters, and particularly on the basis of control parameters produced on the basis of the program parameters. The control device controls the treatment device on the basis of the program parameters, particularly the program parameters that are required by the user and the further program parameters, and particularly on the basis of control parameters produced on the basis of the program parameters.

A method program is understood to mean a control program that determines the specific flow of a treatment according to a predetermined type of treatment and according to a manner stipulated by the user.

Preferably, the user can stipulate the type of treatment of the sample. Such a type of treatment can be used particularly:

for nucleic acid purification, particularly
"MagSep Blood gDNA": purification of genomic DNA from whole blood, particularly by using the Eppendorf® MagSep Blood gDNA kit;
"MagSep Tissue gDNA": purification of genomic DNA from living tissue, particularly by using the Eppendorf® MagSep Tissue gDNA kit;
"MagSep Viral DNA/RNA": purification of viral RNA or DNA from cell-free body fluids, particularly by using the Eppendorf® MagSep Viral DNA/RNA kit;
and for PCR applications, particularly
"Compose Mastermix";
"Normalize Concentrations";
"Create Dilution Series";
"Setup Reactions".

Preferably, the laboratory machine take the type of treatment chosen by the user as a basis for automatically selecting the appropriate set of program parameters, in which the program parameters that are required by the user are then queried by the user in steps (b) and (c). The program parameter set may firstly contain the program parameters that are required by the user and may secondly contain further program parameters. These further program parameters can be stipulated automatically on the basis of the chosen treatment type, or can be stipulated automatically on the basis of at least one, or all, program parameter(s) input by the user, and/or may be stored in the memory device.

The stored parameter sets are preferably in optimized form—or are optimized by the laboratory machine—for the type of treatment, as a result of which the user preferably does not require any special knowledge for optimizing the parameters. The control parameters that are necessary for performing the concrete treatment by means of the treatment device are derived from the program parameter set.

For a type of treatment, a program parameter set of program parameters that are specific to this type of treatment is preferably defined. The program parameters in this program parameter set can define particularly the accessories to be used for the treatment, e.g. sample container, transport container, and/or the tools to be used, and/or further consumables.

The association between program parameter set and type of treatment is stored in the memory device of the laboratory machine. Preferably, the laboratory machine is designed such that the user can store and/or use further such associations in the laboratory machine. This association, in combination with the clearer and well structured querying of the program parameters, makes operation of the laboratory machine particularly efficient. This association is preferably made by the use of one or more program modules, with a respective program module being tailored to a particular application.

Preferably, the laboratory machine has at least one program module, wherein a predetermined program module is used for controlling a predetermined laboratory task for the treatment of laboratory samples,
wherein the treatment is controlled by using a selected program module with which the plurality of program parameters that are chosen at least in part by the user are associated,
wherein the at least one processor device is used particularly for executing at least one program module and wherein the at least one memory device is used for storing the at least one program module,
wherein the at least one control program contains instructions in order to execute steps (a), (b), (c) and (d) on the basis of the selected program module, wherein the program parameters to be queried in step (b) are associated with the selected program module.

It is particularly advantageous if the program module is used by the laboratory machine in order to produce a method that is stipulated by the user. In this case, a program module queries the program parameters that are required by the user in the relevant parameter set that is associated with the program module and the type of treatment, and the user inputs relevant values. The control program then produces, particularly by using the program module and the program parameters associated therewith or the values of said program parameters, the actual control code—indirectly shaped by the user—for controlling the treatment by means of the control parameters, which is also called the method program.

Preferably, the laboratory machine can use a program module and the plurality of program parameters that are chosen at least in part by the user to automatically produce at least one method program that is used for controlling a particular laboratory task for the treatment of laboratory samples, wherein the at least one processor device is used particularly for executing at least one method program and wherein the at least one memory device is used for storing at least one method program, wherein the program parameters to be queried in step (b) are associated with the method program produced by using the selected program module, wherein the at least one control program contains instructions in order to execute step (c2) on the basis of the selected program module:

(c2) production of the method program according to this program module on the basis of the required program parameters, wherein in step (d) the treatment is performed by executing the method program.

Preferably, the control program is designed to allow the desired program module to be selected by the user from the number $NP>=1$ of predetermined program modules via the user interface, wherein the method program associated with the program module is stored or can be stored in the memory device in each case. A method program can thus also be produced outside the laboratory machine and then transferred to the laboratory machine. As an alternative to direct execution, the method program can initially be stored and changed/added to by the user and/or executed at a later time.

Preferably, in step (a) a plurality of query areas are displayed in order to query a plurality of program parameters.

Preferably, in step (a) the program parameters are queried in the form of a query sequence with successively arranged query areas, particularly in the form of a list in which a plurality of query areas are provided, and wherein at least one section of the query sequence or the list is displayed in the first display area. Such data input is particularly clear.

Preferably, the query sequence or the list is in a form such that a query area whose input area has been touched by a user is displayed with a first type of visual highlight in comparison with the other display areas. By way of example, this query area may be presented in a brighter form than the other query areas or in a different colour. This makes the use of the laboratory machine even more convenient.

Preferably, the query sequence or the list is in a form such that a query area in which the user has not yet input a value for a program parameter is displayed with a second type of visual highlight in comparison with the other query areas, e.g. in a different colour. This makes the use of the laboratory machine even more convenient.

Preferably, the query sequence or the list is in the form such that a query area in which the user has already made all inputs for at least one value of at least one program parameter is displayed with a third type of visual highlight in comparison with the other query areas, e.g. in a different colour. This makes the use of the laboratory machine even more convenient.

Preferably, the laboratory machine and/or the control program therefor is/are in a form such that the list can be moved by the user, particularly by touching the first display area, particularly can be scrolled by a gesture, in order to display a different section of the list in the first display area.

Preferably, in step (b) the required program parameters are ascertained via a number $N_T$ of query areas. Preferably, each query area has an associated query number N between 1 and $N_T$, in each case inclusive, wherein this query number is displayed in or next to the query area. This makes the use of the laboratory machine even more convenient.

Preferably, in step (c) the values input by the user for the program parameters are displayed with a piece of information about these program parameters, particularly as an automatically produced text presentation and/or image presentation, called a "scratch list". This increases clarity, and the use of the laboratory machine becomes even more convenient. Preferably, following querying of all program parameters, this scratch list displays all program parameters indicated by the user, preferably further program parameters, in each case preferably with the description, and particularly the "default" values of these program parameters.

Preferably, the relevant query number N is displayed in the scratch list for the at least one value that is input by the user for a program parameter. This increases clarity, and the use of the laboratory machine becomes even more convenient.

Preferably, the at least one program parameter, particularly the program parameter that is required by the user, is selected from the following set of physical variables that are relevant for the treatment of a laboratory sample by means of the treatment device: number of samples, dilution factor, target volume, position of the samples in a sample vessel holder or in a microtitre plate, sample temperature, times and/or time differences, temperatures or temperature differences, rates of change of such parameters, etc.

Preferably, the control program also contains instructions in order to execute the following step:

production of a method program by using the program parameters input by the user, and storage of the method program in the memory device, wherein the method program can be edited by the user. This makes the use of the laboratory machine even more flexible.

The invention also relates to a method for the program-controlled treatment of at least one laboratory sample by means of a laboratory machine by a control program in the laboratory machine, wherein the laboratory machine has at least the following components:

a treatment device for the automatic treatment of the at least one laboratory sample, wherein the treatment is controlled automatically by using a plurality of program parameters that are chosen at least in part by the user, an electronic control device having
a processor device for data processing, particularly for the execution of a control program for controlling the laboratory machine, and
having at least one memory device for storing data, particularly the control program and the program parameters, a user interface device for the manual input of data by a user, and for the display of information, particularly of information that these data contain, wherein the user interface device has a display, particularly a touchscreen display, and this at least one control program for controlling the laboratory machine and performing the method, which has the following steps:

(a) display of at least one query area in a first display area of the display, wherein a query area has at least one information area and at least one input area associated with this at least one information area, (b) progressive querying of program parameters that are required for the execution of the treatment by virtue of a piece of information for the at least one program parameter being displayed in the at least one information area and an input from the user, particularly a touch on the at least one input area, being captured in the at least one input area, (c) in each case following input of at least one program parameter by the user, either immediately following input by the user or after the user has made several inputs, particularly after he has made all inputs required by the user: display of the at least one value that is input by the user for the at least one program parameter in an information area of the second display area of the display, wherein preferably, following the querying of these required program parameters, one, a plurality of, or all value(s) input by the user for these program parameters is/are displayed in this second display area; this conclusively informs the user about the selection at least following the parameter query (d) performance of the treatment by using the queried program parameters.

Further features of the inventive method for the program-controlled treatment of at least one laboratory sample can be found in the description of the inventive laboratory machine.

The invention also relates to a storage medium, particularly an optical, magnetic or electronic data storage medium, having a control program for an inventive laboratory machine that contains instructions in order to carry out the following steps on the laboratory machine:

(a) display of at least one query area in a first display area of the touchscreen display, wherein a query area has at least one information area and at least one input area associated with this at least one information area, (b) progressive querying of program parameters that are required for the execution of the treatment by virtue of a piece of information for the at least one program parameter being displayed in the at least one information area and an input from the user, particularly a touch on the at least one input area, being captured in the at least one input area, (c) in each case following input of at least one program parameter by the user: display of the at least one value that is input by the user for the at least one program parameter in an information area of the second display area of the display, wherein preferably, following the querying of these required program parameters, one, a plurality of, or all value(s) input by the user for these program parameters is/are displayed in this second display area, (d) performance of the treatment by using the queried program parameters.

The invention also relates to the use of the inventive laboratory machine or the inventive method for performing a laboratory task for the treatment of laboratory samples, wherein this laboratory task is chosen particularly from the group containing the following tasks:

nucleic acid purification, particularly
purification of genomic DNA from full blood, particularly by using the Eppendorf® MagSep Blood gDNA kit; this type of treatment is also called "MagSep Blood gDNA";
purification of genomic DNA from living tissue, particularly by using the Eppendorf® MagSep Tissue gDNA kit; this type of treatment is also called "MagSep Tissue gDNA";
purification of viral RNA or DNA from cell-free body fluids, particularly by using the Eppendorf® MagSep Viral DNA/RNA kit; this type of treatment is also called "MagSep Viral DNA/RNA";

and PCR applications, particularly
production of one or more PCT mastermixes from pre-mixes or individual constituents, particularly buffer, polymerase, dNTPs, primers, markers, etc.); in this case, particularly the volume of each required constituent is calculated by the control device, particularly by means of the program module that is associated with the "Compose Mastermix" treatment; this type of treatment is also called "Compose Mastermix";
dilution of at least two DNA/RNA samples in order to obtain the same concentration in all samples; the desired concentrations can be input manually by the user, for example, or imported from a file; this type of treatment is also called "Normalize Concentrations";
dilution of one or more DNA/RNA standard samples with a known concentration in succession in order to produce a calibration curve that can be used for the quantitative PCR; this type of treatment is also called "Create Dilution Series";
production of reaction processes in which a plurality of or many samples are combined with one or more mastermixes. Optionally, it is thus also possible to produce reactions for the replication of DNA/RNA; this type of treatment is also called "Setup Reactions".

The laboratory machine can be altered such that it can be used to perform further types of treatment. This can be accomplished by virtue of the fact that files and/or programs or program parts that are required therefor, particularly a program module associated with the type of treatment, are transferred to the laboratory machine, particularly the memory device thereof, subsequently.

A laboratory sample is a sample that can be treated in a laboratory. Instead of the term laboratory sample, the description of the invention also uses the term "sample". The sample may be a fluid. The sample may be liquid, gelatinous, pulverulent or solid, or may have phases of this kind. The sample may be a mixture of such phases, particularly a liquid mixture, a solution, a suspension, e.g. a cell suspension, an emulsion or dispersion. A solution is a homogeneous mixture of at least two substances. A liquid sample may be one that is usually handled in a biological, chemical, medical laboratory. A liquid sample may be an analysis sample, a reagent, a medium, a buffer, etc. A solution has one or more dissolved solid, liquid or gaseous substances (solutes), and also has a preferably liquid solvent that forms particularly the larger proportion or greatest proportion of the volume than the solution forms. The solvent may itself be a solution.

The treatment of (a) laboratory sample(s) may involve one or more of the following procedures cited below, in particular simultaneously or in succession:

- transport of the laboratory sample, particularly by a transport device, under the action of gravitation and/or force brought about by the laboratory machine;
- contactless (noninvasive) physical treatment of the sample, in particular thermal treatment, particularly heating and/or cooling, in particular regulated temperature control of the sample; or freezing or thawing of the sample, or other thermal prompting of a phase change in the sample, e.g. evaporation, condensation, etc.; magnetic treatment of the sample; optical treatment of the sample, particularly exposure of the sample to radiation, particularly light, in particular visible light, infrared light or UV light, or detection of such radiation, in particular fluorescent light, from this sample; magnetic treatment of a sample with magnetic parts, in particular magnetic separation of magnetic parts, particularly "magnetic beads", from a fluid phase of the sample; movement of the sample, that is to say performance of mechanical treatment on the sample, particularly shaking, rotation, oscillation, vibration, centrifugation, acoustic treatment, particularly with ultrasound, in each case for the purpose of mixing the sample or separating parts within the sample or for transporting the magnetic parts from the sample or into the sample, for example;
- invasive physical treatment of the sample, that is to say performance of mechanical treatment on the sample: introduction of stirring tool, e.g. stirring rod or magnetic flea, into the sample and stirring, introduction of a sonode for acoustic or ultrasonic treatment, introduction of transport means, particularly transport containers, into the sample, e.g. dispenser tip or pipette tip, or cannula or hose; addition of other auxiliaries to the sample;
- chemical, biochemical or biomedical treatment of the sample: addition of chemical (e.g. reactant, reagent, solvent, solute) biochemical (e.g. biochemical macromolecules, e.g. DNA, DNA constituents; pharmaceutical agents), or biomedical (blood, serum, cell medium) substances;
- storage of the sample, particularly for a period defined under program control, particularly under certain physical conditions, e.g. at certain temperature, temperatures or temperature changes, in particular repeated temperature changes, e.g. cyclically and/or periodically repeated temperature changes, and/or setting of an ambient pressure, e.g. application of an overpressure or an underpressure, particularly a vacuum, and/or setting of a defined ambient atmosphere, e.g. an inert gas or a particular humidity, under certain radiation conditions, e.g. screened from visible light, in the dark, or under defined irradiation;
- measurement or analysis of the sample, particularly analysis by noninvasive and/or invasive treatment of the sample, particularly in order to measure at least one or more chemical, physical, biochemical and/or medical properties of the sample; particularly counting of cells by means of cell counters;
- handling of the sample, particularly changes in at least one property of the sample, particularly by means of noninvasive and/or invasive treatment of the sample.

This treatment takes place particularly under program control, by using at least one program parameter.

This treatment takes place particularly on the basis of at least one control parameter, which determines the treatment of the laboratory sample by means of the treatment device. A control parameter can stipulate a period, a time, a particular sample volume and/or metering volume, a particular sample temperature, etc. A control parameter can relate to the automatic use of a particular transport head, of a particular type of transport container, of a particular type of sample containers, of one or more individual samples or of particular positions for these components in the work area. A control parameter can relate to the treatment of an individual sample or to the treatment of a plurality of or many samples.

Preferably, a control parameter is selected automatically by the laboratory machine on the basis of at least one program parameter, in particular is selected automatically on the basis of the program parameters selected by the user. This provides the user with the advantage that he does not need to determine all control parameters individually. The user does not need to have any knowledge about the programming of the machine. Instead, the control parameters that are required for the treatment are selected by means of the program parameters that are input by the user. This makes the use of the laboratory machine particularly convenient.

A control parameter may also correspond to a program parameter.

The transport of a sample may be transport from a sample container to a transport container and/or from a transport container to a sample container or other destination. This transport takes place particularly under program control, by using at least one program parameter.

By way of example, the transport container may be a dispenser container that has a moving piston and an inlet/outlet opening. The piston produces an underpressure or overpressure in the dispenser container and thus sucks the sample into the container or dispenses it again. This procedure follows the displacer principle, i.e. the usually liquid and hence incompressible sample to be moved is moved by force by virtue of the volume previously taken in from the sample being moved by the piston. The piston is usually moved, particularly moved under program control, by a movement device that is associated with the laboratory machine.

The transport container may also be a pipette tip. A pipette tip has an inlet/outlet opening and a second opening. The second opening is coupled to an intake device, as a result of which an underpressure can suck (pipette) a liquid sample from a sample container into the transport container. The sample is dispensed by ventilating the intake area, by means of gravitation and/or via an overpressure that is produced via the second opening in the pipette tip, for example.

The transport container is made preferably in part or completely of plastic. It is preferably a consumable that is typically used only for one treatment or a small number of treatment steps for the sample. Alternatively, the transport container may in part or completely comprise another material.

The transport of a sample may be transport of the sample from a starting position to a destination position. The starting position may be there when the sample is arranged in a first sample container, and the destination position of this sample may be the position thereof in a second sample container into which the sample is transferred. In the present case, this type of transport is also referred to as sample transfer or transfer. In practice, a sample transfer is usually performed in order to transfer a sample from a storage container, for example in which the sample was stored and/or which may contain a larger quantity of the sample, for example, to a second sample container, in which the sample is treated further. This transport takes place particularly under program control, by using at least one program parameter.

The transport container is preferably connected or connectable to a transport device of the laboratory machine.

A sample container may be a single container that contains only a single sample, or may be a multiple container that contains a plurality of single containers connected to one another.

A single container may be an open container or a sealable container. In the case of a sealable container, there may be a cover element, particularly a closure cap. The cover element may be firmly connected to the container, e.g. as a hinged lid or a hinged closure cap, or can be used as separate component.

Preferably, a multiple container has a plurality of single containers arranged in fixed positions relative to one another, particularly arranged in accordance with the crossing points in a grid pattern. This simplifies the automated actuation of the positions and particularly the individual addressing of samples. A multiple container may be in the form of a plate element, in which the single containers are connected such that they form a plate-like arrangement. The single containers may be in the form of depressions in a plate or may be connected to one another via web elements. The plate element may have a frame element in which the single containers are held. These connections for components may be integral connections, i.e. cohesive connections, and/or may be connections produced by a common injection moulding process, or may be produced by force fit and/or form fit. The plate element may be a microtitre plate, in particular.

Multiple containers may have a plurality (from 2 to 10) of single containers. They may also have a multiplicity (greater than 10), typically 12, 16, 24, 32, 48, 64, 96, 384, 1536, of single containers. The multiple container may be a microtitre plate, in particular. A microtitre plate may be designed on the basis of one or more industrial standard(s), particularly the industrial standards ANSI/SBS 1-2004, ANSI/SBS 2-2004, ANSI/SBS 3-2004, ANSI/SBS 4-2004.

The maximum sample volume that can be held by a transport container or a sample container is typically between 0.01 ml and 100 ml, particularly 10-100 µl, 100-500 µl, 0.5-5 ml, 5-25 ml, 25-50 ml, 50-100 ml, depending on the type of transport container or sample vessel chosen.

A sample container may have an information area that may have information about the sample container or about the content thereof. The information area may have coded information, e.g. a bar code or QR code, or an RFID chip, or a differently coded piece of information. The information may have information concerning the identification of the sample and/or of a sample container. The laboratory machine may have an information reading device in order to read this information and preferably to make it available to the control device.

The sample container is made preferably in part or completely of plastic. It is preferably a consumable that is typically used only for one treatment or for a small number of treatment steps for the sample. Alternatively, the sample container may in part of completely comprise another material.

The sample container can preferably be transported using a transport device of the laboratory machine.

The laboratory machine is preferably designed to treat a multiplicity of samples in succession and/or in parallel. In particular, the laboratory machine is preferably designed to treat, in particular to transport, to empty and/or to fill, a multiplicity of sample vessels, in particular single containers and/or multiple containers in a program-controlled manner.

Preferably, the laboratory machine has at least one holding device for at least one sample container, particularly a holding frame for holding a plurality of single containers, called a "sample vessel rack". The holding device is preferably designed to be transportable so as to be able to move within the work area of the laboratory machine, or between different work areas. The holding device can hold a plurality or multiplicity of single containers at a predetermined position of the holding device. This simplifies the individual program-controlled actuation or addressing of sample containers or samples.

A workstation may have auxiliary means for positioning and/or orienting one or more components at this work position. These components may be one, a plurality of, or many single vessels, for example, or may have one or more multiple containers, or may have a holding device for sample vessels. These auxiliary means can be used for connecting these components to the workstation with a force fit and/or form fit. By way of example, the workstation may contain, at predetermined positions in the workstations, as auxiliary means, depressions in the work surface so as to hold elevations on said components as complementary auxiliary means with a form fit therein and thus to bring about positioning and/or orientation.

One or more adapter devices may be provided in order to arrange a first holding device in a predetermined manner on a second holding device or a workstation, particularly to position it and/or orient it therein.

The laboratory machine preferably has at least one work area that may be open to the surroundings or may be partly or completely screened by a housing device. Preferably, the housing device is partially transparent in order to allow the user to observe the procedures taking place under program control in the work area, screened by the housing device.

Preferably, the laboratory machine has precisely one work area. Such a laboratory machine is compact and may be suitable particularly for use on a laboratory bench, in which case it is then particularly also called a bench device. The bench may be the workbench in a chemical, biochemical or biomedical laboratory, for example. The laboratory machine may also be designed for setup in such a laboratory. A laboratory machine with a work area may also be in the form of an independently operating device in such a laboratory, or may be incorporated in/into a complex of devices.

The laboratory machine may also be in the form of a series of laboratory apparatus, in which a plurality of work areas are arranged adjacently such that a transport apparatus can be used to transport one, a plurality or a multiplicity of samples between the work areas in succession and/or in parallel. A work area in a series of laboratory apparatus is preferably designed such that a particular laboratory task, relating usually to the parallel and/or sequential handling of a multiplicity of samples, is performed. This specialization of each work area achieves a high work throughput in the series of laboratory apparatus. In order to perform such a particular task, provision may be made for each work area to involve the performance of only one type of treatment on at least one sample, or only a few types of treatment, e.g. two to ten types of treatment. The transport apparatus may have a rail system and/or a robot device for the program-controlled movement of samples or sample containers.

A laboratory machine may be connected or connectable to a LIMS. LIMS stands for laboratory information and management system. A LIMS is known to be a software system that relates to the data processing in chemical, physical, biological, medical automatic or semiautomatic laboratories. Such data can originate from measurements on the samples and/or may relate to the control of the handling of the data. A LIMS is preferably used for measured value capture and measured value evaluation. LIMS is used to increase the work throughput in a laboratory and/or to optimize the efficiency of the treatment of laboratory samples.

A work area may have a preferably substantially planar, preferably horizontally arranged, work surface. The work area may have a plurality of predetermined workstations. A workstation may be associated with a section of the work area. This association may be permanent or can be determined under program control. A workstation may be permanently configured or may be able to be fitted with different accessories.

The position of the workstations and/or the state of the accessorization of the workstation may be stored as a piece of information in the laboratory machine, particularly the memory device. This information can be used in order to allow the program-controlled treatment of the samples that are arranged at particular positions in the work area and that are intended to be treated on one or more of these workstations.

A workstation can be used to store substances, e.g. to store samples, cleaning agents, waste.

A workstation can be used to store tool elements.

By way of example, a tool element may be a transport head for the transfer of fluid, particularly a pipetting head, which may have a connecting section for connecting a pipette tip (single-channel pipetting head) or for connecting a plurality of pipette tips (multi-channel pipetting head) to the pipetting head. At least one pressure-tight and gas-tight channel that is connected to the pipetting head can be used to suck fluid into the at least one pipette tip when the latter is connected to the connecting section. This pipetting takes place particularly under program control, particularly under the influence of at least one program parameter, in laboratory machines. The transport head may also be a dispensing head that has at least one movement device for moving a piston of the dispensing tip. In laboratory machines, the movement device is moved particularly under program control, particularly under the influence of at least one program parameter. The transport head can be used for metering liquid, particularly for metering in different areas; a transport head may be designed for metering a liquid sample with a volume that may be selected from a volume range that is specific to this transport head: by way of example, 1-50 μL or 20-300 μL, or 50-1000 μL ("l" and "L" are each an abbreviation for liters). A transport head may be in the form of a single-channel head in which only one sample is transported, or may be in the form of a multiple channel, particularly an eight channel or 12 channel, in which a plurality of samples are handled or transported in parallel. Preferably, specific transport containers are provided that are able to be used on the basis of the respective type of transport head, particularly according to the relevant volume range.

By way of example, a tool element may be a transport head for transporting articles, e.g. a carrying and/or gripping tool for carrying and/or gripping an article. A carrying tool may have a mounting section for detachably mounting the article on the carrying tool, e.g. by virtue of the article being connected to the carrying tool by force fit and/or form fit and/or magnetism. This allows within the work surface or between a plurality of work areas and/or work surfaces.

A tool element may also be a treatment unit, e.g. for performing thermal, acoustic, optical and/or mechanical treatment on at least one sample.

A workstation can be used to perform a treatment on laboratory samples. To this end, a treatment unit may be permanently installed on the workstation or may be able to be arranged thereon. This treatment takes place particularly under program control, using at least one program parameter.

A treatment unit for thermal treatment may have a temperature control device in order to adjust the at least one sample to particular temperatures simultaneously or in succession, particularly within stipulated periods of time, and/or to change these temperatures at particular rates. This thermal treatment takes place particularly under program control, using at least one program parameter. This allows a PCR (polymerase chain reaction) to be performed on one, a plurality of or a multiplicity of PCR samples, for example.

A treatment unit for measuring a laboratory sample may have a measuring device. The measuring device may have a detector that measures at least one physical parameter in accordance with at least one physical property of at least one sample. A physical parameter may correspond to an intensity of radiation, particularly to the intensity of a radiation emission from the sample, e.g. the intensity of the fluorescent light from the sample fluorescing under stimulation, particularly on the basis of wavelength, i.e. by capturing a particular spectrum. A physical parameter may correspond to the intensity of radiation transmitted by the sample, a radiation that is scattered or reflected by the sample. The physical parameter may relate to the sample temperature, or to an electrical property of the sample, which may be able to be determined by means of a capacitive measurement, for example, or may be able to be determined by means of a resistance measurement. The measuring device may be able to be controlled by at least one program parameter, and its measured values may be able to be captured particularly via the control device of the laboratory machine, and particularly may be able to be stored as measurement data in the memory device, and/or processed by the processor device.

A treatment unit may have a handling device for handling the at least one sample, particularly in order to perform a treatment on the at least one sample. A handling device can be used for mechanically handling the sample, e.g. moving, e.g. shaking or vibrating, thermal handling or treatment by means of radiation, in order to bring about a (bio)chemical reaction or biological or biomedical state change, e.g. sterilization, in the sample. This handling takes place particularly under program control, particularly by using at least one program parameter.

The laboratory machine may have a transport device for transporting at least one moving head section. The head section may be a transport head for transporting at least one sample and/or for transporting at least one tool element. The head section may have a connecting section for connecting at least one transport container to the transport device.

The transport device may also have a program-controlled movement device, also called a robot device, in order to move the head section and/or the connecting section and particularly, if appropriate, the at least one transport container under program control, particularly in accordance with a movement sequence that is prescribed by the control device, or another control device. This head section may have this connecting section provided on it. In addition, this head section may have the connecting section provided on it for the purpose of connecting a tool element to the head section.

The robot device may have one or more drive devices, e.g. electric motors, in order to allow the program-controlled movement of moving components, e.g. a moving head section, particularly a holding or gripping tool or another moving tool element, e.g. a moving treatment unit. The robot device may have a single-element or multi-element movement arm that allows the transport of the head section, and particularly the transport of samples, between various, preferably freely-selectable, positions in the work area. In addition, the robot device may have a rail system, in which case the head section is mounted on a moving slide or roll element that can be moved by means of this rail system to the positions that are prescribed by the arrangement of the rail system. The movements of the robot device are preferably program controlled, and particularly controlled by at least one program parameter.

The laboratory machine may have an information reading device in order to read a piece of information about a sample and/or a sample container and/or a treatment instruction for this sample and/or this sample container and, preferably, to make it available to the control device of the laboratory machine.

The laboratory machine preferably has at least one metering device. This can preferably be used to meter at least one desired sample volume for the purpose of setting a desired sample volume to be transported. By way of example, the metering device may be formed by virtue of the control device being designed to prompt the transport of a predetermined volume of a sample from a sample container to a transport container and/or from the transport container to a sample container or another destination. By way of example, this is accomplished by the actuation of an intake device in a pipetting device or the actuation of a movement device in a dispensing device, each of which are preferably incorporated in a transport head. This actuation preferably takes place under program control, and particularly under the control of at least one program parameter.

The laboratory machine preferably has at least one timer device and/or preferably a timekeeper device in order to allow the time-dependent treatment of the samples. The time-dependent treatment preferably takes place under program control, and particularly under the control of at least one program parameter.

In one preferred embodiment of the inventive laboratory machine, said laboratory machine is designed to take the type of treatment chosen by the user and the program parameters input by the user as a basis for automatically selecting one or more of the components cited below for use in the program-controlled treatment:
  at least one suitable sample container, in particular suitable for holding a plurality of samples that are intended to be handled together, intended to be mixed, for example, or between which a chemical reaction or biochemical, biological or biomedical interaction is intended to occur;
  at least one suitable transport container, particularly a pipette tip and/or dispenser tip;
  at least one suitable transport head, to which the preferably automatically chosen transport container can be connected,
  at least one suitable tool element that is used for performing the desired treatment.

Preferably, the inventive laboratory machine is designed to take the type of treatment chosen by the user and the program parameters input by the user as a basis for automatically selecting one or more of the control parameters cited below for use in the program-controlled treatment:
  at least one period of time during which a particular work step in the treatment is performed;
  at least one sample volume and/or metering volume;
  at least one work position of the at least one work surface;
  movement parameters for stipulating the required movement sequence in the robot device of the laboratory machine for the desired treatment of the sample.

The automatic selection of the cited components and/or the control parameters on the basis of at least one program parameter, particularly on the basis of the at least one program parameter selected by the user, provides the user with the advantage that he does not need to individually determine the selection of the components and control parameters himself. Instead, the control parameters that are required for the treatment are selected by means of the program parameters input by the user. The user does not need to have any knowledge about the programming of the machine. This makes the use of the laboratory machine particularly convenient.

The automatic selection of the cited components and/or the control parameters on the basis of at least one program parameter makes it possible to achieve the effect that the user information (e.g. 20 samples to be diluted) means that the correct pipetting head is automatically gripped, or more generally the appropriate tool, e.g. transport head and/or tool head, is used. This means that the user does not have to decide what is the optimum tool, but rather he merely decides what his desired treatment is, e.g. nucleic acid purification in a desired manner. The user, e.g. a biologist, a technical biological assistant, a technical medical assistant, then thus merely needs to make the decisions that his training allows him to make easily and quickly, and he does not need to have mastery of an abstract programming language or to undertake relatively long calculations.

The treatment device of the laboratory machine has: preferably at least one work area, preferably at least one transport device, preferably at least one treatment unit.

Preferably, the laboratory machine has the property of permanently storing the program parameters input by the user and later reloading them automatically or when initiated by the user. The user can then change individual instances of the parameters in order to define a type of sample treatment completely. This increases user convenience and reduces susceptibility to error. This is advantageous against the background that laboratory machines are used particularly efficiently for recurring processes.

Further preferred refinements of the inventive laboratory machine and the inventive method can be found in the description below of exemplary embodiment in conjunction with the figures and the description thereof. Identical components in the exemplary embodiments are essentially denoted by the same reference symbols unless described otherwise or evident otherwise from the context. In the figures.

Figure 1:
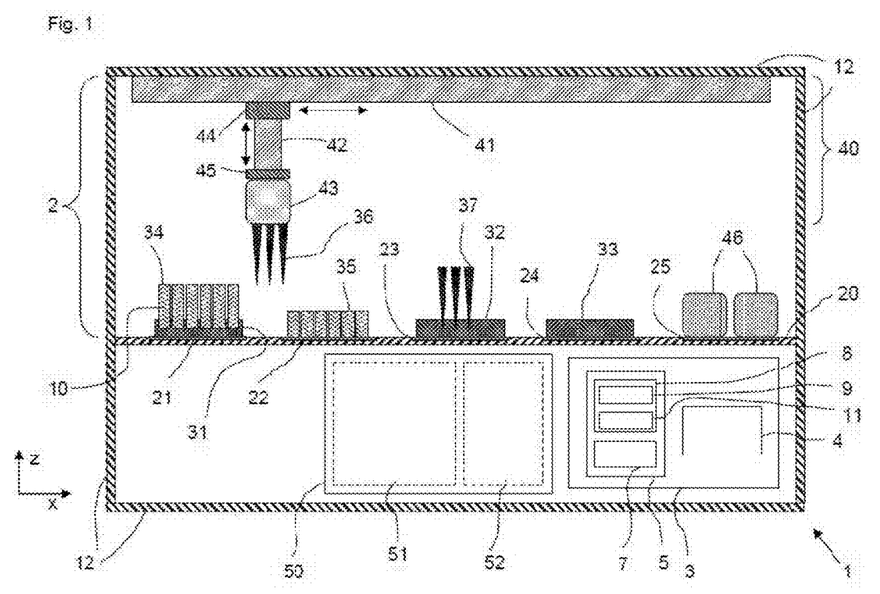
FIG. 1 schematically shows an exemplary embodiment of the inventive laboratory machine.

FIG. 1 shows the laboratory machine 1. The laboratory machine 1 is used for the program-controlled, automatic treatment of liquid laboratory samples 10. The laboratory machine is in the form of a bench appliance. It has a treatment device 2 for performing a treatment according to one or more types of treatment.

The laboratory machine 1 also has an electronic control device 3. This contains a processor device 4 for data processing, this data processing involving the execution of a control program for controlling the laboratory machine and the treatment. The electronic control device 3 also contains at least one memory device 5 for storing data, particularly the control program 7 and the program parameters 8. The program parameters 8 contain the program parameters 9 that the user requires for performing a desired treatment and further program parameters 11, which can be calculated, for example, or are already stored in the laboratory machine, or are transferred to this laboratory machine.

The laboratory machine has a base portion 12 that contains a base plate, a housing frame and a housing device.

Within the context of the description of the invention, horizontal means parallel to the x axis, parallel to the y axis, that is to say perpendicular to the plane of the drawing, and "vertical" means "along the direction of gravitation", i.e. along the z axis. These axes are part of a Cartesian coordinate system x, y, z, as shown in FIG. 1. The positive z axis points toward "the top", and the negative z axis points toward "the bottom", that is to say in the direction of gravitation.

The laboratory machine 1 also has a horizontally arranged work platform with a work area 20, which in this case is in the form of a planar, horizontally arranged work surface 20. This work platform is associated with the treatment device 2 and is used for treating the samples. The work surface has various workstations 21, 22, 23, 24 and 25 arranged on it, specifically in predetermined positions on this work surface. This simplifies the addressing and actuation of positions within a workstation.

The workstation 21 is a surface section of the work area. This has a holding device 31, namely a sample vessel rack 31 for holding a plurality of individual containers, namely test tubes 34, at predetermined positions in the sample vessel rack 31. The holding device 31 is oriented and positioned in a predetermined position on this work surface 20 by means of an auxiliary device (not shown), namely two pins (not shown) on the worktop 20 and two depressions (not shown) on the base of the holding device, into which these pins engage with a form fit. This applies similarly to the positioning of the multiple container 35, which is a microtitre plate, of the holding device 32 for pipette tips 37, of the thermomix device 33, which is used for simultaneously mixing and controlling the temperature of samples, and of the head sections 46, which are mounted on the workstation 25 in order to be automatically actuated and used when required.

The treatment device 2 also has a transport device 40 for transporting the samples. The transport device 40 has a robot device that has a rail device for moving the lift element 42. The rail device is designed to move the head section 43 connected to the lift element 42 parallel to the x direction, specifically by means of the rail element 41, and is designed for movement parallel to the y direction, specifically by means of the rail element 44. The vertical movement of the head section 43 is effected by means of the lift element 42. The robot device has the control device 3 or a second control device associated with it. The (second) control device controls the movement sequence according to which the head section 43 is moved by the transport device 40 during treatment of laboratory samples.

The laboratory machine 1 also has the display 50, which is in the form of a touch-sensitive display ("touchscreen display"). The display has a first display area and a second display area.

The first display area is used for performing a desired treatment, particularly in the following manner: display of at least one query area in the first display area of the display, wherein a query area has at least one information area and at least one input area associated with this at least one information area (step a). In addition: progressive querying of program parameters that are required for the program-controlled execution of the treatment by virtue of a piece of information for the at least one program parameter being displayed in the at least one information area and an input by the user, particularly a touch on the at least one input area, being captured in the at least one input area (step b).

The second display area is used in the following manner: in each case following input of at least one program parameter by the user: display of the at least one value that is input by the user for the at least one program parameter in an information area of the second display area of the display, the querying of these required program parameters being followed by the display of one, a plurality of or all values that are input by the user for these program parameters in this second display area (step c).

Steps a), b) and c) are also described with reference to FIG. 2.

The querying of the program parameters 9 required by the user for treating the sample(s) in the first display area 51 and the display of these program parameters 9 with the description thereof in the second display area 52 are used to allow simple operation of the laboratory machine. In particular, the laboratory machine is designed to derive from program parameters 9 that are input by the user all information and particularly control parameters 104 (see FIG. 3a) that are necessary for performing the treatment that the user desires on the laboratory sample using a control program 101 (see FIG. 3a). The effect achieved by these measures is that the program-controlled laboratory machine 1 can be used for treatments that are defined at least in part by the user, without the user requiring programming knowledge for programming a control program or method program.

On the basis of purely application-related user inputs, the control program produces a suitable process for the treatment of the sample(s), in order to perform the specific desired treatment according to a time of treatment, particularly according to one of several at least partly predetermined types of treatment, the data of which, particularly program parameters and/or software, are already stored in the laboratory machine or can be stored therein subsequently. These user inputs are the program parameters 9, which are already known to the user from the treatments performed in similar fashion manually, which means that operation of the laboratory machine 1 is relatively intuitive for such users. These user inputs relate to or are the number of samples one or more dilution factors, target volumes, positions of the sample(s) in a sample vessel rack 31 or in a multiwell plate 35, for example.

Figure 3A:
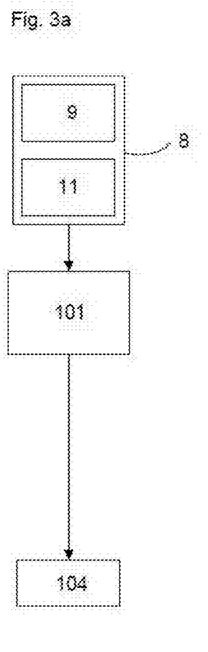
FIG. 3a schematically shows the use of the program parameters, the control program and the control parameters in an inventive laboratory machine for carrying out the inventive method, based on an exemplary embodiment.
Figure 3B:
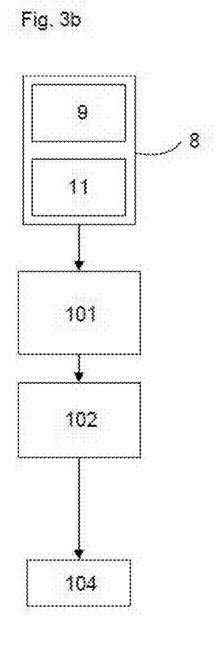
FIG. 3b schematically shows the use of the program parameters, the control program, a program module and the control parameters, based on an exemplary embodiment.

Preferably, each type of treatment that can be performed by the laboratory machine has a program module 102 (see FIG. 3*b*) that is stored in the memory device or can be stored therein subsequently. The program module can control the performance of steps a), b) and c) or can influence them in a manner that is specific to the type of treatment. Finally, the program module 102 can prompt or influence the production of the control parameters 104. Each program module 102 provides a particular, preferably small (e.g. 2 to 15), number $N_T$ of query steps. In these query steps, the user inputs values for at least one program parameter 9. In the last query step, the user can initiate performance of the treatment, with the laboratory machine automatically taking into account the program parameters that are input by the user. The laboratory machine preferably already contains the information or program parameters that is/are required for a standard case of the type of treatment. It performs the treatment without the user needing to perform further optimization operations. Instead, the treatment processes produced by the program modules already contain specific optimizations for critical treatment steps, e.g. relating to the choice of suitable sample containers, transport containers, timings or other parameters. Each program module may have an associated decision tree, according to which the required program parameters 9 are queried according to a branch of the decision tree or a ramification.

The advantage of this automation of the programming of the laboratory machine can be described with reference to the following example: in order to perform a series of dilutions with samples, the work area needs to be provided with suitable accessories, instructions for controlling the processes need to be generated, and the program parameters for these instructions need to be set. For the series of dilutions, there is the disadvantage, in the case of manual performance or in the case of known laboratory machines from the prior art that provide exclusively manually programmable method programs, that the different volumes for the metering commands have to be calculated by the method programmer himself. Conclusive automatic handling requires conditional and unconditional branch commands to be added. This requires suitable programming experience and knowledge about the commands and the manner of operation of the appliance. In preferred refinements of the inventive laboratory machine, the approach is considerably simplified by the cited automatic determination of the control parameters, on the other hand.

Figure 3C:
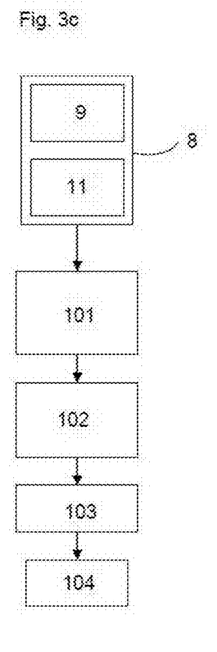
FIG. 3c schematically shows the use of the program parameters, the control program, a program module, a method program and the control parameters, based on an exemplary embodiment.

Preferably, a program module 102 produces a method program 103 (see FIG. 3*c*) that is used as a control program for the specific treatment defined by the user according to the type of treatment chosen by the user, said control program producing particularly all control parameters for automatic performance of this treatment. The laboratory machine may be designed such that the method program can be edited in order to be subsequently altered by the user, or in order to have a method program optionally not automatically written by a program module but rather programmed. This achieves even greater flexibility in the use of the laboratory machine.

The user guidance oriented to the type of treatment by means of steps a) and b) dispenses with the stringing-together of complex commands and the parameterization thereof. In particular, a method program is written from the program module. In this case, the instructions (commands) and program parameters 11 are for the most part prescribed by the relevant type of treatment, or are calculated automatically. The distribution pattern of the respected transfer commands is produced automatically. Further automatic calculations can relate to: the amounts of liquid, container sizes and/or series of dilutions. Sample containers, transport containers, tool elements and/or head sections to be used are ascertained automatically, for example, or are proposed by the laboratory machine.

Figure 2:
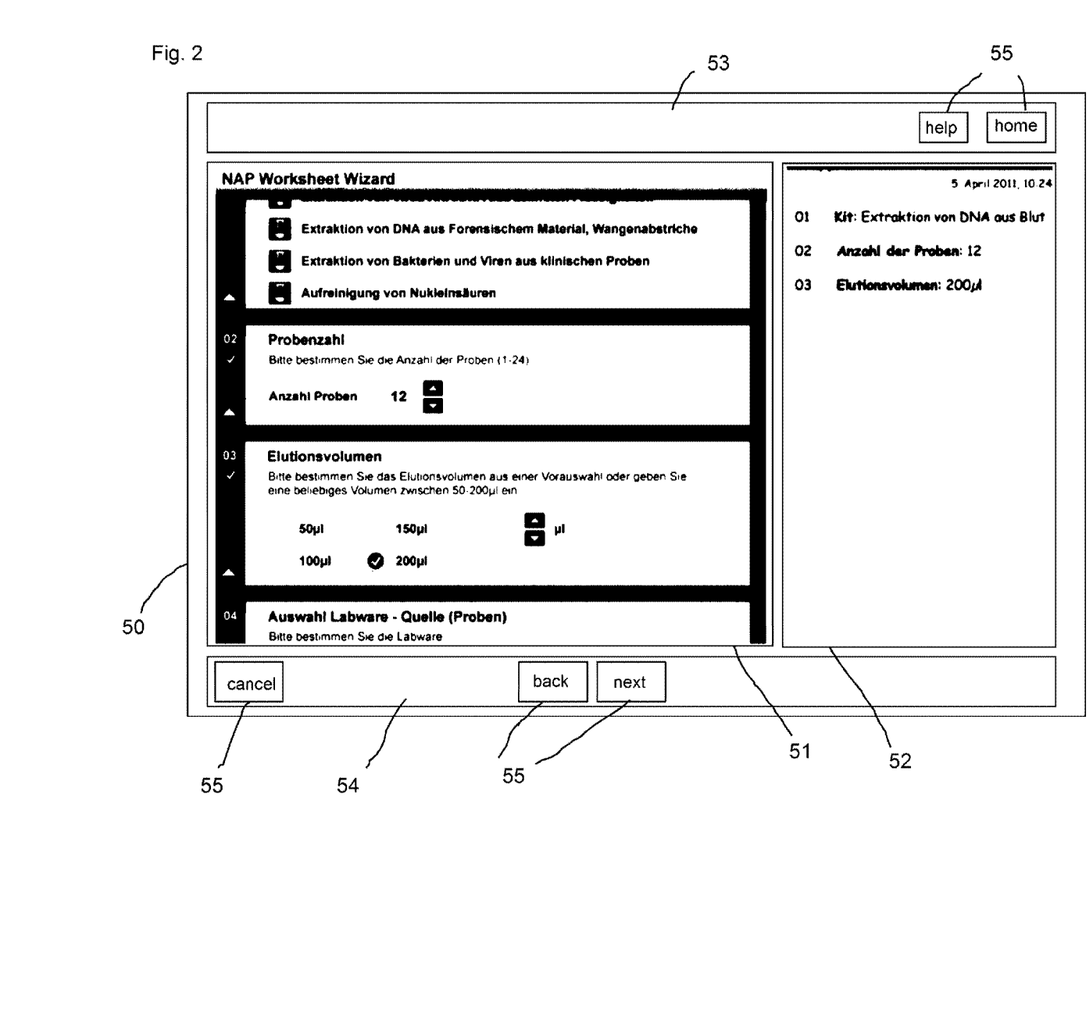
FIG. 2 shows a touchscreen display of the inventive laboratory machine from FIG. 1, with a first display area and a second display area.

FIG. 2 shows the touchscreen display 50 with a first display area 51 and a second display area 52. The query steps take place in the first display area 51 as a query sequence, in this case in the form of a list that can be scrolled in a vertical direction by means of a vertical swipe gesture on a touchscreen. Displayed above the list is a title bar that can reproduce information about the chosen type of treatment, for example, in this case "NAP". The query sequence can also be called a "Wizard". The query steps each have an input area (light area) that has a description of the program parameter to be input or other information, in this case in the form of text, in at least one information area, with the ordinal number N of the query step being displayed next to the respective input area. In FIG. 2, the list has been scrolled such that the input areas for query steps 1 to 4 are at least partially visible, with only the ordinal numbers 2, 3 and 4 being visible. A tick next to the input areas where N=2 and N=3 indicates that a user input has already been made for this query step and the relevant program parameter(s) 9 required by the user has/have already been input. In line with steps b), an input has already been made in the second display area the for a particular query step, in this case shown the ordinal numbers N=1, 2 and 3. In this case, the information is shown on a row-by-row basis and in text form in a second display area: to the left of a row, the ordinal number is shown, e.g. "2", then the description of the program parameter 9, e.g. "number of samples", and then the value that is input by the user for the relevant program parameter, in this case "12", for example.

The touchscreen display 50 may have at least one further display area. In this case, it has a third display area 53 and a fourth display area 54. The further display area may have an input area 55, for example, which is in the form of a button that is used to emulate particularly a knob or lever or the like. In the present case, the third input area is a title bar that can reproduce information about the chosen type of treatment, for example. The third input area also has the "help" and "home" buttons, which can be used by the user to display a piece of help information, particularly for a particular type of treatment and the program parameters thereof, in the display. The "home" button can be used by the user to change to a starting screen, for example in order to change basic settings on the laboratory machine, or to select the type of treatment and to restart the wizard. This display can be provided in the display area, which corresponds at least in part to the first and/or the second display area. The fourth display area 54 is in the form of a base bar and has the "back", "next" and "cancel" buttons 55. The laboratory machine identifies query steps that the user has not yet handled, e.g. by presenting the relevant input areas in semi-transparent or otherwise visually highlighted form.

The invention claimed is:

1. A laboratory machine for the program-controlled treatment of at least one laboratory sample, comprising a treatment device for the program-controlled treatment of the at least one laboratory sample, wherein the treatment is controlled by using a plurality of program parameters that are chosen at least in part by a user, the laboratory machine comprising an electronic control device having at least one processor device for data processing, wherein the data processing involves the execution of at least one control program for controlling the laboratory machine, wherein the program parameters are variables which are set to particular values, wherein the setting of said values influences the controlling of the laboratory machine by the at least one control program, the electronic control device having at least one memory device for storing data, the control program and the program parameters, the laboratory machine comprising a user interface device for the manual input of data by a user, and for the display of information, including the information that said data contain, wherein the user interface device has a display, wherein the at least one control program for controlling the laboratory machine comprises instructions for performing the following steps:

(a) displaying at least one query area in a first display area of the display, wherein said query area has at least one information area and at least one input area associated with said at least one information area;

(b) progressively querying one or more values of the program parameters that are required for the program-controlled execution of the treatment by virtue of a piece of information for the program parameters being displayed in the at least one information area and an input from the user being captured in the at least one input area;

(c) in each case following said input of said value of at least one of said program parameters by the user during the progressive querying in step (b): displaying said at least one value of the at least one program parameter that is input by the user in an information area of a second display area of the display; wherein, following the querying of the required program parameters, a plurality of or all values of these program parameters input by the user are listed in said second display area, the values of the program parameters input by the user being listed with a piece of information about these program parameters as a text presentation and/or image presentation;

(d) performing the treatment by using the queried program parameters;

the laboratory machine having at least one program module, wherein a predetermined program module is used for controlling a predetermined laboratory task relating to the treatment of laboratory samples, the treatment being controlled by using a selected program module with which the plurality of program parameters that are chosen at least in part by the user are associated, the at least one processor device being used for executing at least one program module and wherein the at least one memory device is used for storing the at least one program module, the at least one control program containing instructions in order to execute steps (a), (b), (c) and (d) on the basis of the selected program module, wherein the program parameters to be queried in step (b) are associated with the selected program module;

wherein a program module and the plurality of program parameters that are chosen at least in part by the user can be used to automatically produce at least one method program (103) that is used for controlling a predetermined laboratory task relating to the treatment of laboratory samples;

the at least one processor device being used for executing at least one method program and the at least one memory device being used for storing at least one method program, the program parameters to be queried in step (b) being associated with the method program produced by using the selected program module, the at least one control program containing instructions in order to execute step (c2) on the basis of the selected program module, step (c2) comprising a production of the method program by automatically writing the program code representing the method program according to this program module on the basis of the required program parameters, the treatment in step (d) being performed by executing the method program;

the control program also containing instructions in order to execute the step comprising a production of a method program by using the program parameters input by the user, and storage of the method program in the memory device, wherein the program code of the method program can be edited by the user;

the treatment device performing at least one of: transport of a laboratory sample, pipetting a laboratory sample, thermal, optical, electromagnetic or ultrasonic treatment of a laboratory sample, addition of a chemical to a laboratory sample, and measurement or analysis of a laboratory sample; and wherein the treatment comprises performing a laboratory task chosen from the group containing the tasks of a nucleic acid purification, including the task of purification of genomic DNA from whole blood, also referred to as "MagSep Blood gDNA", the task of purification of genomic DNA from living tissue, also referred to as "MagSep Tissue gDNA", the task of purification of viral RNA or DNA from cell-free body fluids, also referred to as "MagSep Viral DNA/RNA", and the task of PCR applications, including the task of "Compose Mastermix", which means a production of one or more PCR mastermixes from premixes or individual constituents, wherein in this case, the volume of each required constituent is calculated by the control device by means of the program module that is associated with the "Compose Mastermix" treatment, the task of "Normalize Concentrations", wherein in this case, at least two DNA/RNA samples are diluted in order to obtain the same concentration in all samples, wherein the desired concentrations are input manually by the user or imported from a file, the task of "Create Dilution Series", wherein in this case, one or more DNA/RNA standard samples with a known concentration are diluted in succession in order to produce a calibration curve that can be used for the quantitative PCR, and the task of "Setup Reactions", wherein in this case, reaction processes are produced by virtue of a plurality of or a multitude of samples being combined with one or more mastermixes.

2. The laboratory machine according to claim 1, wherein the control program is designed to allow the desired program module to be selected by the user from the number NP>1 of predetermined program modules via the user interface, wherein the method program associated with the program module is stored or can be stored in the memory device in each case.

3. The laboratory machine according to claim 1, wherein in step (a) a plurality of query areas are displayed in order to query a plurality of program parameters.

4. The laboratory machine according to claim 1, wherein in step (a) the program parameters are queried in the form of a list by virtue of a list containing a plurality of query areas being provided, and wherein at least one section of the list is displayed in the first display area.

5. The laboratory machine according to claim 4, wherein the display (50) is a touchscreen display and the list can be moved by the user by touching the first display area in order to display a different section of the list in the first display area.

6. The laboratory machine according to claim 1, wherein in step (b) the required program parameters are ascertained via a number $N_T$ of query areas.

7. The laboratory machine according to claim 6, wherein each query area has an associated query number N between 1 and $N_T$, in each case inclusive, wherein the query number is displayed in the first display area in or next to the query area.

8. The laboratory machine according to claim 7, wherein the relevant query number N and the at least one value that is input by the user for a program parameter are listed in said second display area, the listing being referred to as the scratch list.

9. The laboratory machine according to claim 1, wherein the at least one program parameter is selected from the following set of physical variables that are relevant for the treatment of a laboratory sample by means of the treatment device: number of samples, dilution factor, target volume, position of the samples in a sample vessel holder or in a microtitre plate, sample temperature, times and/or time differences, temperatures or temperature differences, rates of change of said parameters.

10. The laboratory machine according to claim 1, wherein the display is a touchscreen display.

11. The laboratory machine of claim 1, wherein the height of the first display area is the same height as the height of the second display area.

12. The laboratory machine of claim 1, wherein the width of the first display area is greater than the width of the second display area.

13. The laboratory machine of claim 1, wherein the first and the second display areas are displayed when at least one, a plurality of or all parameter(s) required by the user is/are queried, and wherein the first and/or the second display area is/are not displayed, when not querying said program parameters.

14. A method for the program-controlled treatment of at least one laboratory sample by means of a laboratory machine and by a control program in the laboratory machine, the laboratory machine comprising a treatment device for the automatic treatment of the at least one laboratory sample, wherein the treatment is controlled automatically by using a plurality of program parameters that are chosen at least in part by a user, the laboratory machine comprising an electronic control device having a processor device for data processing, wherein the data processing involves the execution of at least one control program for controlling the laboratory machine, wherein the program parameters are variables which are set to particular values, wherein the setting of said values influences the controlling of the laboratory machine by the at least one control program, and the electronic control device having at least one memory device for storing data, the control program and the program parameters, the laboratory machine comprising a user interface device for the manual input of data by a user, and for the display of information, including the information that said data contain, wherein the user interface device comprises a display, wherein the method comprises the following steps performed by the at least one control program for controlling the laboratory machine and performing the sample treatment:

(a) displaying at least one query area in a first display area of the display, wherein said query area has at least one information area and at least one input area associated with this at least one information area;

(b) progressive querying one or more values of the program parameters that are required for the program-controlled execution of the treatment by virtue of a piece of information for the program parameters being displayed in the at least one information area and an input from the user being captured in the at least one input area;

(c) in each case following said input of said value of at least one of said program parameters by the user during the progressive querying in step (b): displaying said at least one value of the at least one program parameter that is input by the user in an information area of a second display area of the display;

wherein, following the querying of these required program parameters, a plurality of or all values of these program parameters input by the user are listed in said second display area, the values of the program parameters input by the user being listed with a piece of information about these program parameters as a text presentation and/or image presentation;

(d) performing the treatment by using the queried program parameters;

the laboratory machine having at least one program module, wherein a predetermined program module is used for controlling a predetermined laboratory task relating to the treatment of laboratory samples, the treatment being controlled by using a selected program module with which the plurality of program parameters that are chosen at least in part by the user are associated, the at least one processor device being used for executing at least one program module and the at least one memory device being used for storing the at least one program module;

the at least one control program containing instructions in order to execute steps (a), (b), (c) and (d) on the basis of the selected program module, wherein the program parameters to be queried in step (b) are associated with the selected program module;

wherein a program module and the plurality of program parameters that are chosen at least in part by the user can be used to automatically produce at least one method program (103) that is used for controlling a predetermined laboratory task relating to the treatment of laboratory samples;

the at least one processor device being used for executing at least one method program and the at least one memory device being used for storing at least one method program;

the program parameters to be queried in step (b) being associated with the method program produced by using the selected program module, the at least one control program containing instructions in order to execute step (c2) on the basis of the selected program module, step (c2) comprising a production of the method program by automatically writing the program code representing the method program according to this program module on the basis of the required program parameters, the treatment in step (d) being performed by executing the method program;

the control program also containing instructions in order to execute the step of a production of a method program by using the program parameters input by the user, and storage of the method program in the memory device, wherein the program code of the method program can be edited by the user;

the treatment device performing at least one of: transport of a laboratory sample, pipetting a laboratory sample, thermal, optical, electromagnetic or ultrasonic treatment of a laboratory sample, addition of a chemical to a laboratory sample, and measurement or analysis of a laboratory sample; and wherein the treatment comprises performing a laboratory task chosen from the group containing the task of nucleic acid purification, including the task of purification of genomic DNA from whole blood, also referred to as "MagSep Blood gDNA", the task of purification of genomic DNA from living tissue, also referred to as "MagSep Tissue gDNA", the task of purification of viral RNA or DNA from cell-free body fluids, also referred to as "MagSep Viral DNA/RNA", and the task of PCR applications, including the task of "Compose Mastermix", which means a production of one or more PCR mastermixes from pre-mixes or individual constituents, wherein in this case, the volume of each required constituent is calculated by the control device by means of the program module that is associated with the "Compose Mastermix" treatment, the task of "Normalize Concentrations", wherein in this case at least two DNA/RNA samples are diluted in order to obtain the same concentration in all samples, the desired concentrations being input manually by the user or imported from a file, the task of "Create Dilution Series", wherein in this case, one or more DNA/RNA standard samples with a known concentration are diluted in succession in order to produce a calibration curve that can be used for the quantitative PCR, and the task of "Setup Reactions", wherein in this case, reaction processes are produced by virtue of a plurality of or a multitude of samples being combined with one or more mastermixes.

15. The method of claim 14, wherein:

purification of genomic DNA from whole blood is performed by providing the materials of an Eppendorf® MagSep Blood gDNA kit and carrying out the respective steps;

purification of genomic DNA from living tissue is performed by providing the materials of an Eppendorf® MagSep Tissue gDNA kit and carrying out the respective steps; and/or purification of viral RNA or DNA from cell-free body fluids is performed by providing the materials of an Eppendorf® MagSep Viral DNA/RNA kit and carrying out the respective steps.

16. A non-transitory computer-readable storage medium having a control program for a laboratory machine, the laboratory machine comprising a treatment device for the automatic treatment of the at least one laboratory sample, wherein the treatment is controlled automatically by using a plurality of program parameters that are chosen at least in part by a user, the laboratory machine comprising an electronic control device having a processor device for data processing, wherein the data processing involves the execution of at least one control program for controlling the laboratory machine, wherein the program parameters are variables which are set to particular values, wherein the setting of said values influences the controlling of the laboratory machine by the at least one control program, and having at least one memory device for storing data, the control program and the program parameters, the laboratory machine comprising a user interface device for the manual input of data by a user, and for the display of information, including the information that said data contain, wherein the user interface device comprises a display, said computer-readable storage medium having a control program comprising instructions in order to execute the following steps on the laboratory machine:

(a) displaying at least one query area in a first display area of the display of said laboratory machine, wherein the query area has at least one information area and at least one input area associated with the at least one information area;

(b) progressively querying one or more values of the program parameters that are required for the program-controlled execution of the treatment by virtue of a piece of information for the program parameters being displayed in the at least one information area and an input from the user being captured in the at least one input area;

(c) in each case following input of at least one of said program parameters by the user during the progressive querying in step (b): displaying said at least one value of the at least one program parameter that is input by the user in an information area of a second display area of the display;

wherein following the querying of these required program parameters, a plurality of or all values input by the user for these program parameters are listed in said second display area, the values of the program parameters input by the user being listed with a piece of information about these program parameters as a text presentation and/or image presentation;

(d) performing the treatment by using the queried program parameters;

the laboratory machine having at least one program module, wherein a predetermined program module is used for controlling a predetermined laboratory task relating to the treatment of laboratory samples, the treatment being controlled by using a selected program module with which the plurality of program parameters that are chosen at least in part by the user are associated, the at least one processor device being used for executing at least one program module and the at least one memory device being used for storing the at least one program module, the at least one control program containing instructions in order to execute steps (a), (b), (c) and (d) on the basis of the selected program module, wherein the program parameters to be queried in step (b) are associated with the selected program module, wherein a program module and the plurality of program parameters that are chosen at least in part by the user can be used to automatically produce at least one method program (103) that is used for controlling a predetermined laboratory task relating to the treatment of laboratory samples;

the at least one processor device being used for executing at least one method program and the at least one memory device being used for storing at least one method program, the program parameters to be queried in step (b) being associated with the method program produced by using the selected program module, and the at least one control program containing instructions in order to execute step (c2) on the basis of the selected program module, step (c2) comprising a production of the method program by automatically writing the program code representing the method program according to this program module on the basis of the required program parameters, the treatment in step (d) being performed by executing the method program;

wherein the control program also contains instructions in order to execute the step of a production of a method program by using the program parameters input by the user, and storage of the method program in the memory device, wherein the program code of the method program can be edited by the user;

the treatment device performing at least one of: transport of a laboratory sample, pipetting a laboratory sample, thermal, optical, electromagnetic or ultrasonic treatment of a laboratory sample, addition of a chemical to a laboratory sample, and measurement or analysis of a laboratory sample; and wherein the treatment comprises performing a laboratory task chosen from the group containing the task of nucleic acid purification, including the task of purification of genomic DNA from whole blood, also referred to as "MagSep Blood gDNA", the task of purification of genomic DNA from living tissue, also referred to as "MagSep Tissue gDNA", the task of purification of viral RNA or DNA from cell-free body fluids, also referred to as "MagSep Viral DNA/RNA", and the task of a PCR applications, including the task of "Compose Mastermix", which means a production of one or more PCR mastermixes from premixes or individual constituents, wherein in this case, the volume of each required constituent is calculated by the control device by means of the program module that is associated with the "Compose Mastermix" treatment, the task of "Normalize Concentrations", wherein in this case, at least two DNA/RNA samples are diluted in order to obtain the same concentration in all samples, the desired concentrations being input manually by the user or imported from a file, the task of "Create Dilution Series", wherein in this case, one or more DNA/RNA standard samples with a known concentration are diluted in succession in order to produce a calibration curve that can be used for the quantitative PCR, and the task of "Setup Reactions", wherein in this case, reaction processes are produced by virtue of a plurality of or a multitude of samples being combined with one or more mastermixes.

17. The non-transitory computer-readable storage medium of claim 16, wherein the display is a touchscreen display.

* * * * *